US00RE46662E

(19) United States
(12) Reissued Patent
Jones et al.

(10) Patent Number: US RE46,662 E
(45) Date of Reissued Patent: Jan. 9, 2018

(54) VASCULAR OCCLUSION DEVICE WITH AN EMBOLIC MESH RIBBON

(71) Applicant: DePuy Synthes Products, Inc., Raynham, MA (US)

(72) Inventors: Donald K. Jones, Dripping Springs, TX (US); Robert R. Slazas, Miami, FL (US); Frederick R. Feller, III, Maple Grove, MN (US)

(73) Assignee: DePuy Synthes Products, Inc., Raynham, MA (US)

(21) Appl. No.: 14/608,624

(22) Filed: Jan. 29, 2015

Related U.S. Patent Documents

Reissue of:
(64) Patent No.: 8,361,104
Issued: Jan. 29, 2013
Appl. No.: 11/663,133
PCT Filed: Sep. 16, 2005
PCT No.: PCT/US2005/033399
§ 371 (c)(1),
(2) Date: Mar. 16, 2007
PCT Pub. No.: WO2006/034150
PCT Pub. Date: Mar. 30, 2006

U.S. Applications:
(60) Provisional application No. 60/610,780, filed on Sep. 17, 2004.

(51) Int. Cl.
*A61F 2/06* (2013.01)
*A61B 17/12* (2006.01)
*A61B 17/00* (2006.01)

(52) U.S. Cl.
CPC .... *A61B 17/12022* (2013.01); *A61B 17/1214* (2013.01); *A61B 17/12113* (2013.01); *A61B 17/12172* (2013.01); *A61B 2017/00867* (2013.01)

(58) Field of Classification Search
CPC ..... A61F 2002/016; A61F 2002/018; A61F 2002/823; A61F 2002/825; A61F 2/00; A61F 2/0077; A61F 2/06; A61F 2/82; A61F 2/852; A61F 2/86; A61F 2/88; A61F 2/885; A61F 2/90–2/92; A61F 2230/0006; A61F 2230/0008; A61F 2230/0013; A61F 2230/005; A61F 2230/0058; A61F 2230/0067; A61F 2230/0069; A61F 2230/0071; A61F 2230/0076; A61F 2230/008; A61F 2230/0091; A61F 2220/0058; A61F 2210/0004;
(Continued)

(56) References Cited

U.S. PATENT DOCUMENTS 5,382,259 A * 1/1995 Phelps et al. ..... 606/151
5,536,274 A * 7/1996 Neuss ..... 623/1.22
5,645,558 A * 7/1997 Horton ..... 606/198
(Continued)

FOREIGN PATENT DOCUMENTS

WO WO 9915116 A1 * 4/1999

*Primary Examiner* — Catherine S Williams
(74) *Attorney, Agent, or Firm* — Nutter McClennen & Fish LLP

(57) ABSTRACT

A vascular occlusion device that includes a central support member that has at least one mesh embolic ribbon extending outwardly from the central support member in the generally radial direction is provided. The mesh embolic ribbon has a collapsed and an expanded configuration.

22 Claims, 3 Drawing Sheets

(58) Field of Classification Search
CPC ..... A61F 2210/0076; A61F 2250/001; A61F 2250/0023
USPC ..... 606/151–158, 191, 198, 200; 128/831; 623/1.11, 1.2
See application file for complete search history.

(56) References Cited

U.S. PATENT DOCUMENTS

| | | | | |
|---|---|---|---|---|
| 5,911,731 | A * | 6/1999 | Pham et al. | 606/191 |
| 5,972,019 | A | 10/1999 | Engelson et al. | |
| 6,019,779 | A * | 2/2000 | Thorud et al. | 606/198 |
| 6,063,111 | A * | 5/2000 | Hieshima et al. | 623/1.22 |
| 6,254,612 | B1 | 7/2001 | Hieshima | |
| 6,280,457 | B1 * | 8/2001 | Wallace et al. | 606/200 |
| 6,361,558 | B1 * | 3/2002 | Hieshima et al. | 623/1.16 |
| 6,425,915 | B1 * | 7/2002 | Khosravi et al. | 623/1.22 |
| 6,494,907 | B1 * | 12/2002 | Bulver | 623/1.22 |
| 6,551,340 | B1 | 4/2003 | Konya et al. | |
| 6,634,361 | B1 * | 10/2003 | Nikolchev et al. | 128/831 |
| 2002/0010481 | A1 | 1/2002 | Jayaraman | |
| 2003/0004568 | A1 * | 1/2003 | Ken et al. | 606/158 |
| 2003/0032976 | A1 | 2/2003 | Boucek | |
| 2003/0139802 | A1 | 7/2003 | Wulfman et al. | |
| 2005/0197687 | A1 | 9/2005 | Molaei et al. | |
| 2006/0020286 | A1 * | 1/2006 | Niermann | 606/200 |

* cited by examiner

VASCULAR OCCLUSION DEVICE WITH AN EMBOLIC MESH RIBBON

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application claims priority to provisional application No. 60/610,780 filed on Sep. 17, 2004, which is hereby incorporated herein by reference.

FIELD OF THE INVENTION

The present invention generally relates to medical devices and methods which are used to occlude vessels within a patient, and more particularly, to occlusion devices which include an embolic mesh ribbon.

BACKGROUND OF THE INVENTION

An aneurysm is an abnormal bulge or ballooning of the wall of a blood vessel. Typically, an aneurysm develops in a weakened wall of an arterial blood vessel. The force of the blood pressure against the weakened wall causes the wall to abnormally bulge or balloon outwardly. One detrimental effect of an aneurysm is that the aneurysm may apply undesired pressure to tissue surrounding the blood vessel. This pressure can be extremely problematic especially in the case of a cranial aneurysm where the aneurysm can apply pressure against sensitive brain tissue. Additionally, there is also the possibility that the aneurysm may rupture or burst leading to more serious medical complications including mortality.

When a patient is diagnosed with an unruptured aneurysm, the aneurysm is treated in an attempt to reduce or lessen the bulging and to prevent the aneurysm from rupturing. Unruptured aneurysms have traditionally been treated by what is commonly known in the art as "clipping." Clipping requires an invasive surgical procedure wherein the surgeon makes incisions into the patient's body to access the blood vessel containing an aneurysm. Once the surgeon has accessed the aneurysm, he or she places a clip around the neck of the aneurysm to block the flow of blood into the aneurysm which prevents the aneurysm from rupturing. While clipping may be an acceptable treatment for some aneurysms, there is a considerable amount of risk involved with employing the clipping procedure to treat cranial aneurysms because such procedures require open brain surgery.

More recently, intravascular catheter techniques have been used to treat cranial aneurysms because such techniques do not require cranial or skull incisions, i.e., these techniques do not require open brain surgery. Typically, these techniques involve using a catheter to deliver embolic devices to a preselected location within the vasculature of a patient. For example, in the case of a cranial aneurysm, methods and procedures, which are well known in the art, are used for inserting and guiding the distal end of a delivery catheter into the vasculature of a patient to the site of the cranial aneurysm. A vascular occlusion device is then attached to the end of a pusher member which pushes the occlusion device through the catheter and out of the distal end of the catheter where the occlusion device is delivered into the aneurysm.

Once the occlusion device has been deployed within the aneurysm, the blood clots on the occlusion device and forms a thrombus. The thrombus forms an occlusion which seals off the aneurysm, preventing further ballooning or rupture. The deployment procedure is repeated until the desired number of occlusion devices are deployed within the aneurysm. Typically, it is desired to deploy enough coils to obtain a packing density of about 20% or more, preferably about 35% and more if possible.

The most common vascular occlusion device is an embolic coil. Embolic coils are typically constructed from a metal wire which has been wound into a helical shape. One of the drawbacks of embolic coils is that they do not provide a large surface area for blood to clot thereto. Additionally, the embolic coil may be situated in such a way that there are relatively considerable gaps between adjacent coils in which blood may freely flow. The addition of extra coils into the aneurysm does not always solve this problem because deploying too many coils into the aneurysm may lead to an undesired rupture.

Therefore, there remains a need that is recognized and addressed according to the present invention for an occlusion device which provides a greater surface area to promote the clotting of blood, and also effectively occupies the space between adjacent occlusion devices without increasing the risk of rupturing the aneurysm.

SUMMARY OF THE INVENTION

The present invention generally relates to vascular occlusion devices and methods for making and using the same. The vascular occlusion devices of the present invention may be associated with a standard delivery catheter system and deployed to a preselected site within the vasculature of a patient using techniques and professional methods generally known in the art.

In one preferred embodiment of the present invention, the vascular occlusion device includes a support wire which has been formed into a helical shape, for example the shape of a standard embolic coil. The occlusion device also includes at least one mesh embolic ribbon, and more preferably a pair of opposed thin mesh embolic ribbons. The embolic ribbons extend outwardly from the support wire in a generally radial direction, and are preferably twisted into a spiral pattern along the length of the support wire.

In another preferred embodiment of the present invention, the occlusion device comprises a hollow tubular central support element which includes a pair of thin mesh embolic ribbons extending from the tubular support element in a generally radial direction. Preferably, the tubular support element and the mesh ribbon material are a unitary structure. In yet another preferred embodiment, a central support element is not required, and the thin mesh ribbon material can be self-supporting. In this embodiment, the occlusion device comprises a mesh ribbon which is preferably twisted into a cork-screw-like or spiral configuration, and then wound into a helical coil.

The occlusive devices of the present invention can be made by winding a support wire around a cylindrical mandrel having semicircular shaped grooves into which the support wire nests. Deposition techniques that are generally known in the art are employed to coat the mandrel and support wire with a thin metal film, such as a nickel-titanium alloy, specifically a nitinol. The thin metal film is then separated, such as by laser-cutting, to form a pair of metal mesh ribbons. The mandrel is removed, and the support wire is stretched in the longitudinal direction to uncoil the support wire. Next, the support wire is twisted about the longitudinal axis of the support wire to form the mesh ribbons into a spiral pattern. The support wire is then formed into the desired shape, preferably a helically wound coil.

Therefore, it is an object or aspect of the present invention to provide a vascular occlusion device that provides a large surface area for the promotion of blood clotting.

It is also an object or aspect of the present invention to provide methods of making an occlusion device having mesh embolic ribbons.

Other aspects, objects and advantages of the present invention will be understood from the following description according to the preferred embodiments of the present invention, specifically including stated and unstated combinations of the various features which are described herein, relevant information concerning which is shown in the accompanying drawing.

BRIEF DESCRIPTION OF THE DRAWINGS

In describing the preferred embodiments of the present invention, reference will be made to the accompanying drawings, wherein.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The occlusion devices of the present invention are generally designed to be delivered to a preselected site within a vessel of a patient by using standard deployment systems, such as TRUFILL® DCS ORBIT™ (Cordis Corporation) hydraulic detachable coils deployment systems, other mechanical, electrolytic or thermal systems or the like, or any other deployment systems or techniques that may be developed in the future. For convenience and simplicity, the following description of the present invention will be described in terms of a vascular occlusion device. However, it will be understood that the description herein should not be considered to limit the invention to only endovascular procedures.

Figure 1:
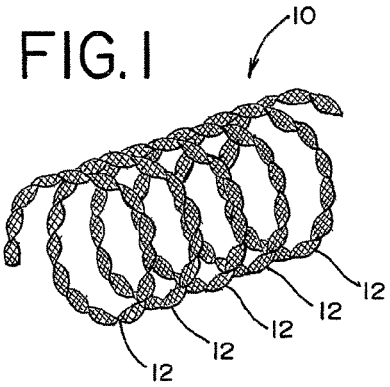
FIG. 1 is a perspective view of a preferred embodiment of the occlusion device of the present invention.
Figure 2:
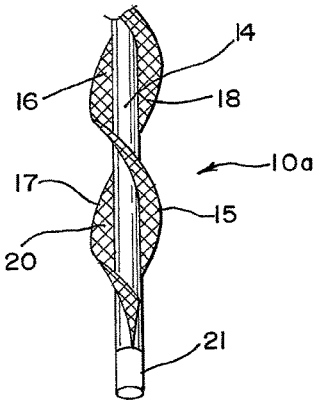
FIG. 2 is an enlarged partially sectioned view of an embodiment of the occlusion device having a support wire.

FIG. 1 generally illustrates a preferred embodiment of the vascular occlusion device of the present invention. The vascular occlusion device, generally designated at 10, is preferably helically shaped to form coils 12. As illustrated in FIG. 2, in one embodiment, the occlusion device 10a includes a center support element, illustrated as a support wire 14. A first embolic mesh ribbon 16 and a second embolic mesh ribbon 18 are located on the support wire 14 and extend from the support wire in a generally radial direction. The mesh ribbons 16, 18 may be deposited on the support wire 14, as in the method described below, or may be attached by a biocompatible adhesive, weld or solder. The first embolic mesh ribbon 16 and the second embolic mesh ribbon 18 may be configured into any simple or complex shape, and are preferably twisted into a spiral pattern around the support wire 14. In an alternative embodiment, the occlusion device 10 may include only one embolic ribbon located on the center support element.

The support wire 14 preferably comprises a metal, and has a diameter between about 0.0005 inch (about 0.013 mm) and about 0.004 inch (about 0.1 mm). The support wire is preferably wound into a helical shape having an overall diameter of between about 0.005 inch (about 0.13 mm) and about 0.015 inch (about 0.38 mm). Suitable metals for the support wire include, but are not limited to, stainless steel, platinum, gold or nitinol. The wire may be configured into a variety of different shapes, such as helical coils, spheres, ellipses, spirals, complex curves or the like. Preferably, the wire is configured into a helical coil. When the support wire is made from a nitinol or other shape memory alloy, the support wire may transition between a martensitic state and an austenitic state, and may be heat treated into any variety of desired shapes, as mentioned above.

More preferably, the support wire is comprised of a radiopaque material to aid in the accurate placement of the occlusion device 10a within the vasculature of a patient. Such radiopaque material may include platinum, tungsten or gold. The material of the support wire 14 may also be any other suitable material, such as a thin polymer wire or tube. Radiopaque material can be included in the form of a ring or rings of any useful shape.

The first and second embolic mesh ribbons 16, 18 are preferably comprised of a thin metal film having apertures 20 extending through the film. The mesh may also be a braided mesh which is formed from a multifilament braid. Preferably, the size of the apertures 20 is between about 5 microns and about 100 microns, and more preferrably between about 10 microns and about 50 microns. The thickness of each embolic ribbon 16, 18 may range from about 5 to about 250 microns, and is preferably between about 10 microns and about 20 microns. When the embolic ribbons are comprised of a thin film material, such as a thin film of nitinol, the thickness of the thin film is preferably between about 0.1 and 250 microns and typically between about 1 and 30 microns. More preferably, the thickness of the thin film is between about 1 to 10 microns or at least about 0.1 microns but less than about 5 microns. The width extending from the outer edge 15 of the first ribbon 16 to the outer edge 17 of the second ribbon 18 is preferably between about 0.012 inch (about 0.3 mm) and about 0.015 inch (about 0.38 mm) in the spiraled shape. In general, the sizing of the device can be varied as needed to be properly accommodated by catheters or devices by which they can be delivered.

In one embodiment, the embolic mesh ribbons 16, 18 are comprised of metal having shape memory and super elasticity such as a nickel-titanium alloy, and more specifically a nitinol. However, as may be appreciated, the embolic mesh ribbons may also be fabricated from any other suitable metal, such as stainless steel, platinum, tungsten or the like, or any suitable biocompatible material, such as a polymer.

Preferably, the embolic mesh ribbons may be transformed between a collapsed state and an expanded state. Such transformable feature is especially advantageous when the embolic mesh ribbons 16, 18 are fabricated from nitinol, or any other suitable shape memory material. In the collapsed state the embolic ribbons 16, 18 may be collapsed inward toward the support wire, so as to lessen the overall cross-sectional width (diameter for circular configurations) of the occlusion device 10. In the expanded state (which can be seen in FIG. 2), the embolic ribbons 16, 18 may extend outwardly from the support wire in a generally radial direction, expanding the overall cross-sectional width of the occlusion device 10 and increasing the overall surface area available for blood to clot thereto.

In this embodiment, the width of each of the embolic ribbons may be any size as long as the overall size of the occlusion device is sized to fit within the desired sized delivery catheter when the ribbons are in the collapsed state. The transition between the collapsed state and the expanded state is preferably temperature activated, and the ribbon preferably transitions between the collapsed state and the expanded state between a temperature of about 30 degrees C. and about 40 degrees C., and more preferably at about the patient's body temperature during the procedure.

When the ribbons are comprised of nitinol, the ribbons may be martensite, or the ribbons may be austenite with a transition from martensite to austenite. If the ribbons are designed to remain martensitic, the configuration of the ribbon in the martensitic state is preferably the expanded position, as illustrated in FIG. 2. Alternatively, the configuration of the ribbons in the martensitic state can be any desired configuration, depending on the intended use. If the ribbons are designed to transition between the martensitic state and the austenitic state, the ribbons may be heat treated so that the ribbons are in the expanded state while austenitic. Alternatively, the ribbons may be heat treated to form any other desired simple or complex austenitic state configuration. While martensitic, the ribbons may be of any configuration, and preferrably are collapsed inward toward the support element.

Figure 3:
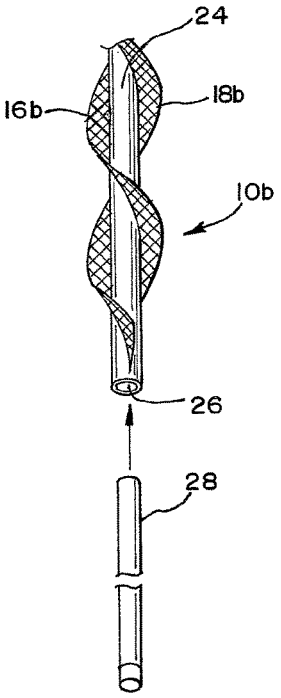
FIG. 3 is an enlarged partially sectioned view of another embodiment of the occlusion device of the present invention.

FIG. 3 illustrates another preferred embodiment of the occlusion device of the present invention. In this embodiment, the occlusion device 10b includes a central tubular support element 24 having a hollow inner channel 26 which may extend through the entire length of the tubular support element 24. A pair of opposed embolic mesh ribbons 16b, 18b, which are of the generally same construction as described above, extend outwardly from the tubular support element 24 in a generally radial direction. The tubular support element 24 and the mesh ribbons 16b and 18b are preferably of a unitary structure. However, it is contemplated that the tubular support element 24 and the embolic ribbons 16b, 18b may be of different structures that are attached together by any suitable attachment means, such as by a biocompatible adhesive, weld or solder.

A support wire 28, similar to support wire 12, may be inserted into the channel 26 of the tubular support member 24 to strengthen the structure of the occlusion device 10b. This embodiment provides for various processing options. For example, the ribbons and the support wire may be heat treated separately, typically before the support wire 28 is inserted into the channel 26. Each then can have different properties due to their respective different materials and/or due to heat treatment differences. This can be especially beneficial when the ribbons 16b, 18b and the support wire 28 are made of nitinol and are in different states due to heat treatment variations.

Figure 4:
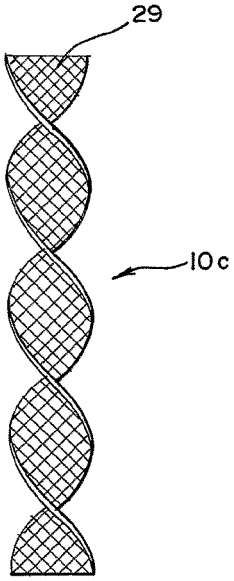
FIG. 4 is an enlarged partially sectioned view of yet another embodiment of the occlusion device of the present invention.

Yet another embodiment of the vascular occlusion device of the present invention is illustrated in FIG. 4. In this embodiment, the occlusion device 10c comprises a mesh ribbon material 29 that is self-supporting, eliminating the need for a central support element. The mesh ribbon 29 may be made of any of materials as described above with respect to mesh ribbons 16, 18. The mesh ribbon 29 is preferably twisted to form a spiral or cork-screw-like configuration, and then wound into a helical shape, as illustrated in FIG. 1. Alternatively, the mesh ribbon 29 may be shaped into any desired simple or complex configuration. When the occlusion device 10c is comprised of a nitinol, it may be designed to remain in a martensitic state, or it may be designed so that it transitions between a martensitic and an austenitic state.

In addition to the features described herein, the vascular occlusion devices of the present invention may also include one or more bioactive materials, such as fibrous materials, foam materials, coatings, therapeutic agents, thrombogenic agents, non-thrombogenic agents, growth factors and the like. Additionally, the occlusion devices of the present invention may also include an attachment location for releasably attaching to a deployment system, such as an attachment head 21 located at the end of support wire 14, as illustrated in FIG. 2.

The occlusion devices described herein are designed to be deployed to a preselected site within a vessel of the body. In treating an aneurysm, a delivery catheter is guided through the vasculature system of a patient to the site of an aneurysm using standard techniques and professional methods generally known in the art. When the ribbons have the feature of being transitioned between a collapsed state and an expanded state, the vascular occlusion device is releasably attached to the distal end of a pusher element with the ribbons in the collapsed state. The pusher element pushes and guides the vascular occlusion device through the delivery catheter to the site of the aneurysm. The vascular occlusion device is guided out of the distal end of the delivery catheter into the aneurysm. The vascular occlusion device is released from the distal end of the pusher. Once inside the aneurysm, the vascular occlusion device may take the form of a variety of simple and complex shapes and configurations, and the mesh embolic ribbons transition into the expanded state. The mesh embolic ribbons increase the amount of space the vascular occlusion device occupies, and thereby increases the surface area onto which the blood can clot and form a thrombus.

This method may be repeated until the desired number of occlusion devices are deployed within the aneurysm. The expanded mesh ribbons fill the space within the aneurysm, and the mesh ribbons are preferably flexible and elastic so that the mesh ribbons may yield to pressure from surrounding occlusion devices and/or the wall of the vessel. The flexible and elastic characteristics of the mesh ribbons allow the mesh ribbons to fill in the space between adjacent occlusion devices without creating a high-pressure situation, and thus reducing the risk of a rupture.

Figure 5:
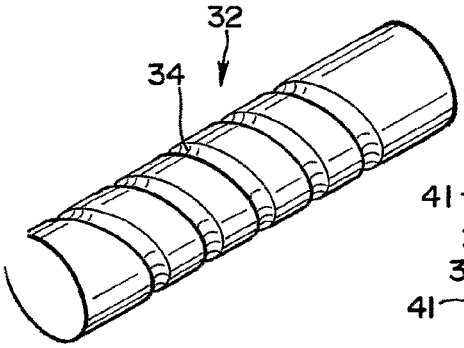
FIG. 5 is a perspective view of a mandrel which can be used in a method to make occlusion devices of the present invention.
Figure 6:
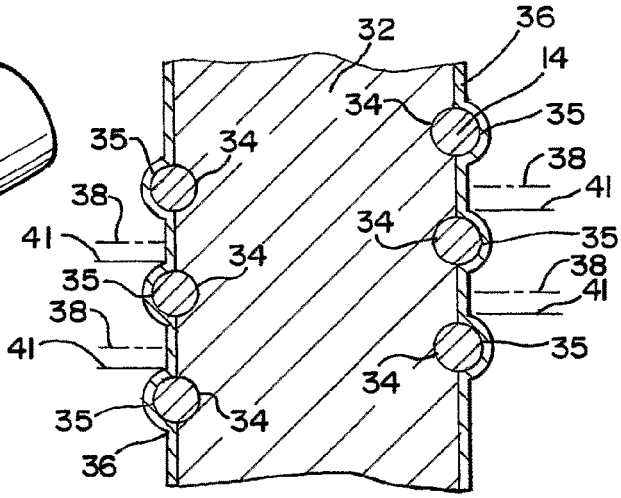
FIG. 6 is a partial cross-section view of the mandrel of FIG. 5 shown with a support wire and a coating of metal film.

The occlusion devices of the present invention may be made by many different methods. The following method can be used to make an embodiment of the present invention. As illustrated in FIG. 5, a mandrel or core 32 may be provided with a semicircular spiral groove 34. As illustrated in FIG. 6, a support wire 14 is wound around the mandrel 32 creating adjacent coils 35. The support wire 14 is wound so that the support wire nests within the grooves 34, leaving about half of the exterior surface of the support wire 14 exposed. The mandrel 32 and the support wire 14 are then coated with a thin film of metal 36 preferably by using deposition and sputtering devices and techniques which are generally known in the art. The thin metal film 36 is preferably a nickel-titanium metal alloy, such as a nitinol. Alternatively, the thin metal film may be any other suitable metal, such as stainless steel, platinum, tungsten or the like.

After the mandrel 32 and support wire 14 have been coated with the thin metal film 36, the thin metal film 36 is then cut with a laser or mechanical means or conventional process between adjacent coils 35 at lines 38 to create a pair of opposed ribbons. The thin metal film may be cut at a location equidistant between the adjacent coils 35 to create ribbons of substantially the same width. Alternatively, the thin metal film may be cut closer to one coil to create ribbons of different size width. If only a single ribbon is desired, the thin metal film may be cut at a location adjacent to one of the coils, as illustrated at cut lines 41. Next, the thin metal film 36 is perforated by a laser or mechanical means or conventional process to form a mesh.

Once the thin metal film 36 has been cut and perforated or otherwise formed into a mesh material, the mandrel 32 is removed. The mandrel 32 is preferably made of copper and is removed by dissolving the copper mandrel in acid. However, the mandrel 32 may be made of any suitable material and may be removed by any suitable method generally known in the art. It is preferred that the mandrel 32 be removed after the thin film 36 has been cut and perforated. However, it will be understood that the order of performance of cutting the thin film, perforating the thin film and removing the mandrel may occur in any desired order.

Figure 7:
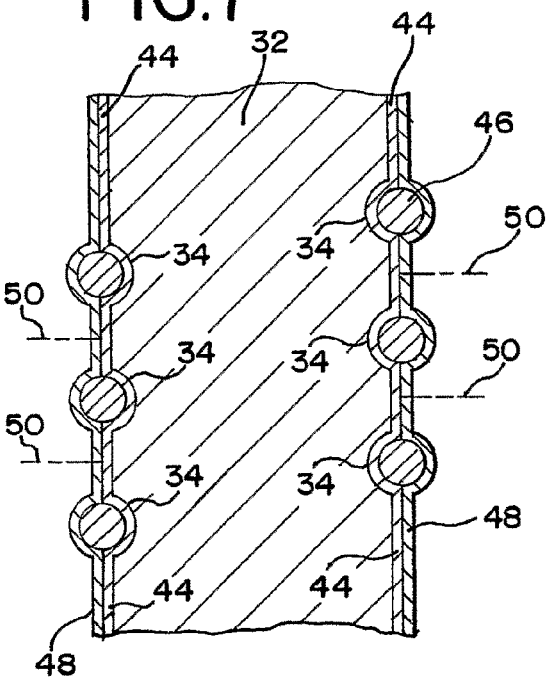
FIG. 7 is a partial cross-sectional view of the mandrel of FIG. 5 shown with a base wire wound around the mandrel and a first and second layer of thin metal film.
Figure 8:
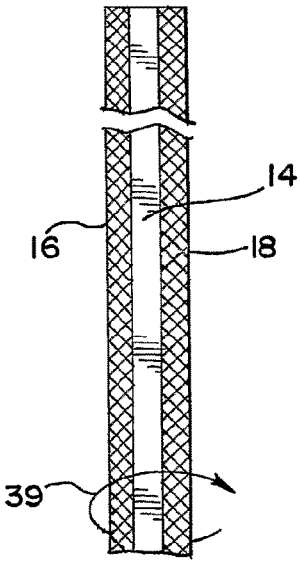
FIG. 8 is an enlarged partial side view of an occlusion device of the present invention prior to being twisted and helically wound.

After the mandrel 32 has been removed, such as by dissolving, the support wire 14 is stretched axially into the shape shown in FIG. 8. The support wire 14 is then twisted relative to the longitudinal axis of the support wire, as indicated at 39 in FIG. 7, to form the ribbons 16, 18 into a spiral pattern.

If the ribbons 16, 18 are made of a thermal shape memory alloy, such as a nitinol, the ribbons may now be heat treated to set the desired shape. The support wire 14 is then wound, preferably onto a mandrel (not shown), to shape the support wire into a helix, as generally illustrated in FIG. 1. Alternatively, the support wire 14 may be configured into any simple or complex configuration.

In another method which may be followed for making occlusion devices of the present invention, referring to FIG. 7, the mandrel 32 is coated with a first thin metal film 44 preferably by employing sputtering and deposition techniques and devices that are generally known in the art. The first thin metal may be comprised of any of the above mentioned suitable metals. A base wire 46 is wound around the coated mandrel 32 so that the base wire nests within grooves 34 having the metal film coating 44. A second layer of thin metal film 48, which may comprise a material different from or the same as the first thin metal film 44, is coated onto the first layer of thin metal film 44 and the base wire 46 where wire 46 is positioned over the film 44.

Both the first and second layers of thin metal film 44, 48 are cut along lines 50 to form a pair of ribbons. Alternatively, the film can be severed to form a single ribbon, in substantially the same manner as described above. The ribbons or ribbon may then be perforated in substantially the same manner as described above.

The mandrel 32 and the base wire 46 are then removed from the assembly. Preferably, the mandrel 40 and the base wire 46 are comprised of copper and are removed by dissolving the base wire and the mandrel in an acid. However, the mandrel 32 and the base wire 46 may be made of any suitable material and may be removed by any suitable method generally known in the art.

Dissolving the base wire 46 creates a center support tube with a lumen extending the length of the support tube similar to the device shown in FIG. 3. The occlusion device is now stretched and twisted relative to the longitudinal axis of the support tube to form the ribbons into a spiral pattern. At this point, if desired, the structure of the occlusion device may be strengthened by inserting a support wire into the lumen and attaching the support wire to the support tube. If the wire is made of a shape memory alloy, such as a nitinol, the wire may be heat treated to set the desired configuration before being inserted into the support tube. Alternatively, the wire and the ribbon material may be heat treated together. The occlusion device may now be configured into the desired shape. Preferably, the occlusion device is wound around a mandrel (not shown) to shape the occlusion device into a helical coil, as shown in FIG. 1.

Figure 9:
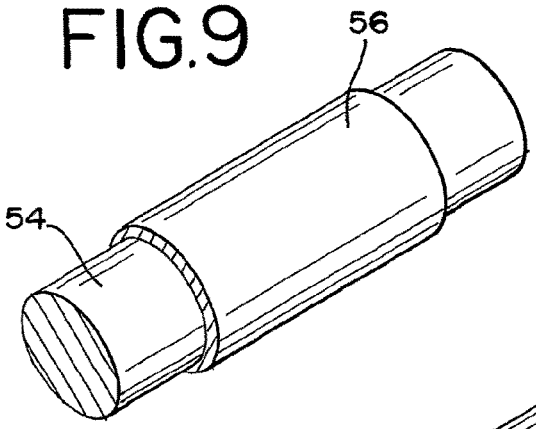
FIG. 9 is a perspective view of a mandrel coated with a thin film as a step in making devices according to an embodiment as illustrated in FIG. 4.
Figure 10:
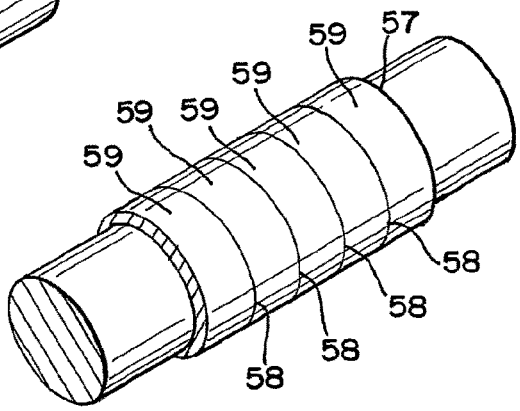
FIG. 10 is a perspective view of the mandrel of FIG. 9 after the thin film has been severed in a subsequent step.
Figure 11:
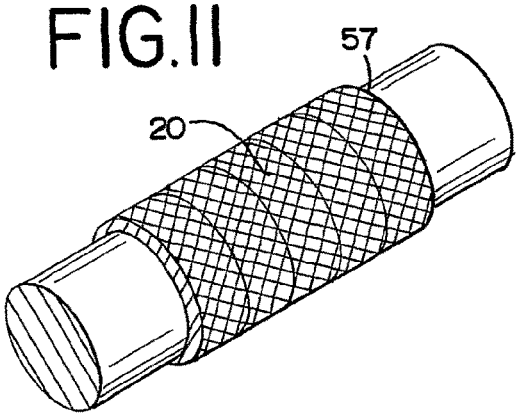
FIG. 11 is a perspective view of the mandrel of FIG. 10 after the thin film has been perforated to form a mesh.

In yet another method of making the occlusive device of the present invention, referring to FIG. 9, a mandrel 54 is coated with a thin film 56 preferably by employing sputtering and deposition techniques and devices known in the art. The thin metal may be comprised of any of the above mentioned suitable metals. Referring to FIG. 10, the thin film 56 is then cut along lines 58, in substantially the same manner as described above, to form a ribbon 57 that is coiled around the mandrel and has adjacent coils 59. The ribbon 57 is then perforated, in substantially the same manner as described above, to form a mesh having slots or apertures 20, as illustrated in FIG. 11.

Figure 12:
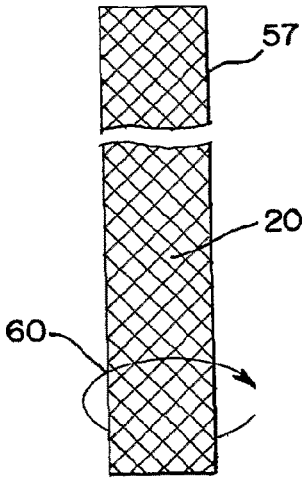
FIG. 12 is a perspective view of the ribbon before the ribbon is shaped into the desired configuration.

The mandrel 54 then is separated from the ribbon 57 in any suitable manner. Preferably, the mandrel 54 is made of copper and is separated from the ribbon 57 by dissolving the mandrel in acid. The ribbon 57 is stretched axially into the shape illustrated in FIG. 12. If the ribbon is made from a shape-memory alloy metal, such as a nitinol, the ribbon may be shaped into the desired configuration and heat treated. Preferably, the ribbon is twisted, as generally designated at 60, to form a spiral pattern as illustrated in FIG. 4, and wound into a coil, as illustrated in FIG. 1, or otherwise formed into a desired shape of the occlusion device or the like.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

[1. An occlusion device comprising:

a central support member having a length and a cross-sectional width, the central support member is wound into a helically shaped coil; and at least one embolic ribbon extending from the central support member in a generally radial direction, said at least one embolic ribbon also extending at least partially along the length of the central support member, wherein the at least one embolic ribbon is shaped into a spiral pattern around the central support member.]

[2. The occlusion device of claim 1 wherein the central support member comprises a wire.]

[3. The occlusion device of claim 1 wherein the central support member comprises a hollow tubular structure.]

[4. The occlusion device of claim 1 wherein the central support member is integral with the at least one embolic ribbon.]

[5. The occlusion device of claim 1 wherein the cross-sectional width of the central support member comprises a diameter.]

[6. The occlusion device of claim 1 wherein the at least one embolic ribbon is comprised of a metal.]

[7. The occlusion device of claim 6 wherein the metal is a shape memory alloy.]

[8. The occlusion device of claim 1 wherein the at least one embolic ribbon comprises a mesh.]

[9. The occlusion device of claim 8 wherein the at least one embolic ribbon comprises a substrate, and the mesh is formed by a plurality of apertures extending through the substrate.]

[10. The occlusion device of claim 8 wherein the mesh is formed from a braided element.]

[11. The occlusion device of claim 1 wherein the at least one embolic ribbon has a collapsed state and an expanded state.]

[12. The occlusion device of claim 11 wherein a transformation between the collapsed state and the expanded state is temperature activated.]

[13. The occlusion device of claim 12 wherein the transformation between the collapsed state and the expanded state is activated at approximately body temperature.]

[14. The occlusion device of claim 1 wherein the at least one embolic ribbon comprises a pair of opposed embolic ribbons.]

15. A vascular occlusion device, comprising:

an embolic coil formed from a support wire of a selected length wound into a helical shape; and a pair of opposed mesh embolic ribbons located on the support wire, said pair of mesh embolic ribbons extending along at least a portion of the length of the support wire and extending outwardly from the support wire *such that each mesh embolic ribbon has an outer edge*, wherein the mesh embolic ribbons are shaped into a spiral around the support wire*;*

*wherein at least one of the opposed mesh embolic ribbons has a thickness greater than about 0.1 microns but less than about 5 microns*.

16. The vascular occlusion device of claim 15 wherein the pair of opposed mesh embolic ribbons comprise a metal.

17. The vascular occlusion device of claim 16 wherein the metal is a shape memory metal.

18. The vascular occlusion device of claim 15 wherein each of the opposed mesh embolic ribbons comprises a substrate with apertures extending therethrough.

19. The vascular occlusion device of claim 15 wherein each of the opposed mesh embolic ribbons comprises a braided element.

20. The vascular occlusion device of claim 15 wherein each of the opposed mesh embolic ribbons includes a collapsed state and an expanded state.

[21. The vascular occlusion device of claim 15 wherein at least one of the opposed mesh embolic ribbons has a thickness greater than about 0.1 microns but less than about 5 microns.]

22. An occlusion device, comprising:

an embolic mesh ribbon, said ribbon twisted *about a longitudinal axis of said embolic mesh ribbon* into a spiral-like pattern as a spiraled ribbon length; and said spiraled ribbon length is helically coiled into the occlusion device.

23. The occlusion device of claim 22 wherein the ribbon comprises a metal.

24. The occlusion device of claim 23 wherein the metal is a shape memory alloy.

25. The occlusion device of claim 23 wherein the shape memory alloy is a nitinol.

26. A method of making an occlusion device, comprising;

winding a support wire around a mandrel in a helical fashion to form adjacent coils;

coating the support wire and the mandrel with a thin metal film;

cutting the thin metal film between the adjacent coils to create at least one embolic ribbon extending from the support wire;

perforating the pair of opposed embolic ribbons;

separating the support wire and thin metal film from the mandrel;

shaping the support wire and the pair of opposed embolic ribbons into a desired shape;

twisting the support wire relative to a longitudinal axis of the support wire to form the at least one embolic ribbon into a spiral shape; and winding the support wire into a helical shape.

27. The method according to claim 26 wherein the winding comprises winding the support wire around a copper mandrel and the separating comprises dissolving the copper mandrel in acid.

28. The method according to claim 26 wherein the separating comprises dissolving the mandrel away.

29. The method according to claim 26 wherein the shaping includes uncoiling the support wire by stretching the support wire along the longitudinal axis of the support wire.

30. The method according to claim 26 wherein the coating comprises coating the mandrel and the support wire with a thin shape memory alloy film; and further including heat-treating the thin shape memory alloy film at said desired shape.

31. The method according to claim 26 wherein the coating comprises sputtering and depositing a thin metal film.

32. The method according to claim 26 wherein the cutting comprises cutting the thin metal film between the adjacent coils to create a pair of opposed embolic ribbons.

*33. A vascular occlusion device, comprising:*

*a central support member having a length and a diameter; and*

*an embolic braided mesh having a thickness and a width that is greater than the thickness, the width of the embolic braided mesh extending in a direction generally aligned with the diameter of the central support member;*

*wherein the embolic braided mesh is positioned on at least a portion of the length of the central support member.*

*34. The occlusion device of claim 33, further comprising an attachment head for releasably attaching to a deployment device.*

*35. The occlusion device of claim 34, wherein the attachment head is located at an end of the central support member.*

*36. The occlusion device of claim 33, wherein the device moves between a collapsed state in which the device is elongate for insertion into a vessel and an expanded state in which the device takes a shape that increases an amount of space the occlusion device occupies.*

*37. The occlusion device of claim 36, wherein the shape is spherical.*

* * * * *